United States Patent
Jo et al.

(10) Patent No.: US 7,351,422 B2
(45) Date of Patent: Apr. 1, 2008

(54) HEMOSTATIC SOLUBLE CELLULOSE FIBERS CONTAINING COAGULATING PROTEIN FOR TREATING WOUND AND PROCESS FOR PRODUCING THE SAME

(75) Inventors: Yoshio Jo, Tokyo (JP); Motonori Aoshima, Tokyo (JP); Koji Tanabe, Tokyo (JP); Koichi Matsushita, Tokyo (JP); Toshiki Inoue, Tokyo (JP)

(73) Assignee: Hogy Medical Co., Ltd., Minato-ku, Tokyo (JP)

( * ) Notice: Subject to any disclaimer, the term of this patent is extended or adjusted under 35 U.S.C. 154(b) by 1014 days.

(21) Appl. No.: 10/069,561

(22) PCT Filed: Feb. 22, 2001

(86) PCT No.: PCT/JP01/01285

§ 371 (c)(1),
(2), (4) Date: Oct. 22, 2001

(87) PCT Pub. No.: WO01/62278

PCT Pub. Date: Aug. 30, 2001

(65) Prior Publication Data

US 2002/0156498 A1 Oct. 24, 2002

(30) Foreign Application Priority Data

Feb. 22, 2000 (JP) .............................. 2000-043786

(51) Int. Cl.
*A61F 2/00* (2006.01)
*A61K 9/00* (2006.01)
*A61K 9/70* (2006.01)
*A61K 35/12* (2006.01)
*C08B 11/00* (2006.01)

(52) U.S. Cl. .................. 424/426; 424/400; 424/423; 424/529; 424/530; 514/2; 514/21; 530/382; 536/84; 536/85; 536/86; 536/91; 536/95; 536/96; 536/98; 536/99; 536/100

(58) Field of Classification Search ............... 424/423, 424/426, 529, 530, 362, 400; 514/21, 2; 530/382; 536/85, 84, 86, 91, 95, 96, 98, 536/99, 100

See application file for complete search history.

(56) References Cited

U.S. PATENT DOCUMENTS 2,510,355 A * 6/1950 Waldeck (Continued)

FOREIGN PATENT DOCUMENTS

EP    0 956 869 A2 * 11/1999

(Continued)

*Primary Examiner*—Michael G. Hartley
*Assistant Examiner*—Simon J. Oh
(74) *Attorney, Agent, or Firm*—Dilworth & Barrese, LLP (57) ABSTRACT

Proposed is a novel soluble trauma-healing and hemostatic cellulose fiber capable of absorbing and readily dissolving hemorrhaging trauma loci when applied thereto and of promoting the hemostatic action of blood platelets and fibrin and cell adhesion to the trauma site. The coagulation protein-containing soluble trauma-healing and hemostatic cellulose fiber is produced in that after treatment of a natural or regenerated cellulose fiber with an aqueous sodium hydroxide solution, said fiber is carboxymethylated by reaction with a monochloro acetic acid solution for a given time (hours) in such a manner that the degree of partial substitution of the glucose units constituting the cellulose molecule (etherification degree) is 0.5-less than 1.0% and that, furthermore, the coagulation proteins fibrinogen, thrombin, and coagulation factor XIII are imparted by surface application or chemical bonding.

38 Claims, 2 Drawing Sheets

(A): In the absence of soluble trauma-healing and hemostatic cellulose fiber (control)
(B): In the presence of soluble trauma-healing and hemostatic cellulose fiber containing 1% of coagulation protein
(C): In the presence of soluble trauma-healing and hemostatic cellulose fiber containing 1% of coagulation protein prepared by the surface application method
(D): In the presence of soluble trauma-healing and hemostatic cellulose fiber containing 1% of coagulation protein prepared by the chemical bonding method.

U.S. PATENT DOCUMENTS

| | | | |
|---|---|---|---|
| 4,091,205 A * | 5/1978 | Onda et al. | 536/85 |
| 4,265,233 A * | 5/1981 | Sugitachi et al. | 128/156 |
| 4,340,731 A * | 7/1982 | Colombo et al. | 536/87 |
| 4,655,211 A | 4/1987 | Sakamoto et al. | |
| 4,752,466 A | 6/1988 | Saferstein et al. | |
| 5,292,362 A | 3/1994 | Bass et al. | |
| 5,420,250 A | 5/1995 | Lontz | |
| 5,631,011 A | 5/1997 | Wadstrom | |
| 5,962,026 A * | 10/1999 | Edwardson et al. | 424/529 |
| 6,200,587 B1 * | 3/2001 | Soe et al. | 424/423 |

FOREIGN PATENT DOCUMENTS

| | | | |
|---|---|---|---|
| EP | 956869 | | 11/1999 |
| JP | 3057446 | | 4/2000 |
| JP | 2000-256958 A | * | 9/2000 |
| WO | 96/17633 | | 6/1996 |
| WO | 96/40174 | | 12/1996 |
| WO | 97/44015 | | 11/1997 |

* cited by examiner

Fig. 1

(A): In the absence of soluble trauma-healing and hemostatic cellulose fiber (control)
(B): In the presence of soluble trauma-healing and hemostatic cellulose fiber containing 1% of coagulation protein
(C): In the presence of soluble trauma-healing and hemostatic cellulose fiber containing 1% of coagulation proteinprepared by the surface application method
(D): In the presence of soluble trauma-healing and hemostatic cellulose fiber containing 1% of coagulation protein prepared by the chemical bonding method.

Fig. 2

(A)
In the absence of soluble trauma-healing hemostatic cellulose fiber

(B)
In the presence of soluble trauma-healing hemostatic cellulose fiber (C)
In the absence of soluble trauma-healing hemostatic cellulose fiber containing coagulation protein prepared by surface application (D)
In the presence of soluble trauma-healing hemostatic cellulose fiber containing coagulation protein prepared by chemical bonding

HEMOSTATIC SOLUBLE CELLULOSE FIBERS CONTAINING COAGULATING PROTEIN FOR TREATING WOUND AND PROCESS FOR PRODUCING THE SAME

BACKGROUNDS OF THE INVENTION

1. Field of the Invention

The invention according to the present application relates to soluble trauma-healing blood-stilling cellulose containing coagulation protein and a method of preparation thereof, and more specifically to an internally absorbing soluble wound-covering blood-stilling material promoting blood coagulation and vascular dilation on application to the internal or external lesion and a method of preparation thereof.

2. Description of the Related Art

In the past there types of traumato-hemostatic agent, namely cellulose oxide, gelatin and micro-fibrous collagen, have been known and have already been used as medical preparations and for medical instruments. Cellulose oxide agents achieve their hemostatic action in that the anhydrous polygluconic acid has an extremely strong affinity to hemoglobin and forms a salt with it. This hemo-coagulation promoting effect is due not so much to the agent's action on the blood's coagulation mechanism but rather to physical action. That is to say, that this agent promotes the formation of blood coagulates as the result of the perfusion of blood causing this agent to swell with the development of brown or black gelatin clots. The agent thus displays an ancillary localized hemostatic action and is absorbed in approximately two weeks. Furthermore, microfibrous collagen contains as the main component natural collagen extracted from the bovine dermis and achieves a hemostatic action through platelet agglutination on contact with blood.

Since the cellulose oxide agent does not directly act on the blood coagulation system it has a weak coagulating effect and thus requires approximately two weeks to be completely absorbed in the system so that it acts as an inflammation and adhesion promoting factor in the affected area during this period. Gelatin agents have a slower absorption than cellulose oxide and are animal derived materials so that there is a considerable possibility of their causing various infectious diseases, including mad cows disease and Kreutzfeld Jakob disease. Moreover, microfibrous collagen takes about a month or longer to be completely absorbed so that it is liable to cause inflammation and adhesion in the affected part during this period. Since the agent is of bovine origin there it carries a risk of infectious diseases such as mad cows disease or or other infections due to unknown viruses.

Hemostasis with the conventional methods using the above hemostatic agents is apt to lead to inflammation and adhesion due to the poor internal absorption of these agents and carries a risk of disease due to unknown infections.

Furthermore, the Japanese Patent Laid-Open No. Hei10-77571 refers to a soluble cellulose fiber whose hydroxyl groups in the glucose units constituting the cellulose molecules of the natural or regenerated cellulose fibers have been partially carboxymethylated so that its etherification degree becomes 1.0% or higher and which exhibits a hemostatic effect by covering the trauma by rapidly dissolving on contact with blood and congealing to a gelatin with the blood.

When the degree of replacement of the carboxymethyl radicals (etherification degree) equals or exceeds 1.0%, however, the agent will not rapidly dissolve even when coming in contact with blood and a large amount of unusable material will remain without exhibiting a significant hemostatic effect, while, furthermore, the solubilized carboxymethyl cellulose fibers have no effect whatsoever on the enzymes of the blood coagulation system such as coagulation factor XII.

Furthermore, the Japanese Patent Application No. Hei11-58412 refers to a soluble trauma-healing hemostatic cellulose fiber whose hydroxyl groups in the glucose units constituting the cellulose molecules of the natural or regenerated cellulose fibers have been partially carboxymethylated so that its carboxymethyl substitution level (etherification degree) becomes 0.5-under 1.0%.

The aforesaid soluble trauma-healing hemostatic cellulose fiber material does rapidly dissolve on contact with blood to exhibit a very potent hemostatic effect it has a blood-stilling effect only when coming in contact with blood. Its effect is thus due to its interactions with the platelets and fibrin of the blood so that in minor hemorrhage, that is to say, in loci (trauma sites) with little platelet and fibrin amounts it has a small hemostatic effect.

SUMMARY OF THE INVENTION

In order to overcome the above difficulties, the inventors of the present application have conducted intensive investigations and found that soluble trauma-healing hemostatic cellulose fiber containing coagulation protein has a superior absorbency in tissue fluids, including blood, is readily dissolved on contact with blood, and even when the coagulation cascade is not active, it will exhibit a hemostatic effect due to stimulation of the agglutination reaction of fibrin monomer which is formed from fibrinogen by the action of the thrombin present in the coagulation protein-containing soluble trauma-healing hemostatic cellulose fiber and as a result of the stabilization of the agglutinates through a cross-linking reaction of the coagulation factor XIII that is contained in said soluble trauma-healing hemostatic cellulose fiber. In other words, the coagulation protein-containing soluble trauma-healing hemostatic cellulose fiber accelerates the agglutination of fibrin monomer formed through the action of thrombin regardless of the activation of the enzymes involved in the coagulation cascade reaction and, furthermore, promotes the adhesion and agglutination of the platelets to the trauma locus due to the rapid dissolving thereof on contact with the blood or body fluids present in the trauma site. It has thus been found to promote the adhesion activity of the fibronectin cells.

Thus, the invention according to this application refers to a material obtained by the application of coagulation proteins to a natural or regenerated cellulose fiber whose hydroxyl groups in the glucose units constituting the cellulose molecule have been partially carboxymethylated in such a manner that the carboxymethyl substitution level (etherification degree) becomes 0.5-under 1.0%, and relates to a material consisting of a coagulation protein-containing soluble trauma-healing hemostatic cellulose fiber obtained by a process in which, after treatment of the natural or regenerated cellulose fiber in sodium hydroxide, the hydroxyl groups of the glucose units constituting the cellulose molecule are partially carboxymethylated by allowing said fiber to react with a monochloroacetic acid for a certain reaction time, preferably 4-18 hours, in such as manner that the substitution level (etherification degree) becomes 0.5-under 1,0% with subsequent purification and in which, furthermore, the refined product is imparted with fibrinogen, thrombin and coagulation factor XIII as the coagulation proteins with subsequent drying.

The coagulation proteins are imparted by way of application to the aforesaid carboxymethylated natural or regenerated cellulose fiber or by way of chemical boding to the aforesaid carboxymethylated natural or regenerated cellulose fiber (that is to say, a means other than the physical bonding brought about by surface application).

Moreover, surface application of the coagulation proteins may be accomplished in practice, by way of example, by spraying a solution containing said coagulation proteins on to the aforesaid carboxymethylated natural or regenerated cellulose fiber. In this event, the coagulation proteins may be applied singly in a combination consisting of all of the three proteins referred to herein above, namely, fibrinogen, thrombin and coagulation factor XIII, or individually in successive order by first applying fibrinogen, then thrombin and finally the coagulation factor XIII.

In contrast, chemical bonding of the coagulation proteins maybe accomplished, byway of example, by chemical reaction involving the addition of a solution containing said coagulation proteins to the aforesaid carboxymethylated natural or regenerated cellulose fiber which has been treated with a carbodiimide reagent. In this event, the coagulation proteins may be added for chemical reaction singly in a combination consisting of all of the three proteins referred to herein above, namely, fibrinogen, thrombin and coagulation factor XIII, or individually in successive order by first adding for chemical bonding fibrinogen, then thrombin and finally the coagulation factor XIII.

Furthermore the invention according to the present application refers to a product obtained by pulverizing the aforesaid carboxymethylated natural or regenerated cellulose fiber imparted with the coagulation proteins as described herein above after imparting said coagulation proteins thereto and after drying. Said powder may be obtained by pulverizing the aforesaid natural or regenerated cellulose fiber imparted with the three coagulation proteins, namely, fibrinogen, thrombin and coagulation factor XIII, in combination by single application or chemical bonding or, alternatively, by pulverizing the aforesaid natural or regenerated cellulose fiber imparted with the three coagulation proteins, namely, fibrinogen, thrombin and coagulation factor XIII, in successive order by consecutive application or chemical bonding with the subsequent mixing thereof.

Moreover, in accordance with the invention of this application, the aforesaid natural or regenerated cellulose fiber imparted with the three coagulation proteins is a drawn thread array consisting of a number of single threads loosely twisted together or a woven fabric produced either by plain-weaving or twill-weaving a drawn thread array consisting of a number of single threads loosely twisted together, whereby the thickness of the drawn thread array corresponds to a Denier number comprised between 20-100.

Furthermore, the invention according to the present application relates to a gauze-like product obtained by converting the aforesaid natural or regenerated cellulose fiber to a wool either before or after imparting the coagulation proteins thereto.

Furthermore, the invention according to the present application relates to product obtained by pulverizing, after imparting said coagulation proteins, the aforesaid natural or regenerated fibers in the form of a drawn thread area or a woven fabric or a gauze.

Moreover, the invention according to this application relates to a product consisting of coagulation protein-containing soluble trauma-healing blood-stilling cellulose fiber prepared in the manner afore-described with an enhanced hemostatic healing effect when applied to the trauma site.

Moreover, the preferred coagulation protein-containing soluble trauma-healing blood-stilling cellulose fiber in accordance with the invention of the present application-may be represented by the following summary Chemical formula 1 or Chemical formula 2 as the structural units constituting the cellulose. Chemical formula 1 represents the arrangement in which the coagulation proteins have been imparted by surface application and Chemical formula 2 an arrangement in which the coagulation proteins have been imparted by chemical bonding.

BRIEF DESCRIPTION OF THE DRAWINGS

FIG. 2 shows in (A) the coagulation rate/time dependence obtained by measuring the platelet coagulation condition in the absence of soluble trauma-healing hemostatic cellulose fiber, in (B) the coagulation rate/time dependence obtained by measuring the platelet coagulation condition in the presence of soluble trauma-healing hemostatic cellulose fiber, in (C) the coagulation rate/time dependence obtained by measuring the platelet coagulation condition in the absence of soluble trauma-healing hemostatic cellulose fiber containing coagulation protein prepared by the application method, and in (D) the coagulation rate/time dependence obtained by measuring the platelet coagulation condition in the absence of soluble trauma-healing hemostatic cellulose fiber containing coagulation protein prepared by the chemical bonding method.

DESCRIPTION OF THE PREFERRED EMBODIMENTS

The following descriptions use embodiments of the practical preparation of the soluble trauma-healing hemostatic cellulose containing coagulation protein and examples of tests for achieving the trauma-healing and hemostatic effects.

As an example for the execution of the preparation of the soluble trauma-healing hemostatic cellulose, the Japanese Patent Application No. Hei11-58412 describes a method for the preparation of soluble trauma-healing hemostatic cellulose whereby 70 g of natural or regenerated cellulose fiber formed into a fabric obtained by drawing an array of 20 loosely twisted fibers and by one-two twill-weaving the drawn fiber array with a thickness of 40 Denier, was introduced into a 1000 mL rotary reaction vessel to which were added 250 mL of sodium hydroxide—ethanol solution consisting of 38 volume parts of a 45% aqueous sodium hydroxide solution and 62 volume parts of 95% ethanol, with subsequent thorough impregnation and stirring for 2 hours at 25 degrees C. Following this, addition was made to this reaction solution of 210 mL of a monochloro acetic acid reaction solution consisting of 40 volume parts of monochloro acetic acid and 60 volume parts of 95% ethanol, with subsequent stirring for 4-18 hours. After the reaction had reached completion, the hydrogen ion index (pH value) of the solution containing the fibers thus obtained was adjusted to 7.0 with 20% hydrochloric acid, whereupon the fibers were washed with a 60-95% aqueous ethanol solution until the sodium chloride content of the fibers we 1% or less. The cellulose fiber treated in this manner was then dried and sterilized to obtain a soluble trauma-healing hemostatic cellulose with the target etherification degree (level of carboxymethyl group substitution) of 0.5-1.0%. The "soluble trauma-healing hemostatic cellulose fibers" mentioned in the test examples below shall be interpreted as the soluble trauma-healing hemostatic cellulose fibers obtained by the afore-described means, unless where specifically stated otherwise.

Next, in test example 1, the etherification degree corresponding to the stirring time with the monochloro acetic acid reaction solution was determined in order to ascertain that the degree of etherification (carboxymethyl group substitution) of the soluble trauma-healing hemostatic cellulose fibers thus obtained was within the range of 0.5-1.0%. The measurement method was such that 1 g of each of the soluble trauma-healing hemostatic cellulose fibers produced by stirring with the monochloro acetic acid solution 2, 4, 8, 14, and 18 hours, respectively, in the aforesaid test example was cut into fine pieces, transferred into a tapering triangular (50 mL) flask, added with 25 mL of anitricaid-methanol solution (using a solution prepared by mixing 100 mL of methanol and 10 mL of nitric acid), shaken for 1 hour and used as the hydrogen type sample. Following this, the sample was trapped by absorptive filtration in a glass filter (G3), washed with 120 mL (three times using 40 mL each time) with an 800 g/L aqueous methanol solution (mixture of 100 mL of anhydrous methanol and 20 mL of water), and finally washed with 25 mL of anhydrous methanol, whereupon the sample was passed through an absorption filter and the sample on the filter was dried at 105 degrees C. for 2 hours. Furthermore, 0.2 g of the hydrogen type sample was accurately weighed, placed in a (100 mL) tapering triangular flask, added with 8 mL of 800 g/L methanol and 20 mL of a standard 0.1 mol/L sodium hydroxide solution and shaken for 30 minutes at 25 degrees C. to convert the hydrogen type sample to the sodium type. Moreover, the excess sodium hydroxide was then determined by titration with a sulfuric acid of a known titer of 0.05 mol/L using phenolphthalein as the indicator in order to determine the etherification degree therefrom. Table 1 below presented the measurement results.

TABLE 1

| Denier number of soluble trauma-healing hemostatic cellulose fibers | Degree of etherification (Carboxymethyl Group Substitution) Stirring Reaction Time (hr) | | | | |
|---|---|---|---|---|---|
| | 2 | 4 | 8 | 14 | 18 |
| 1 | 0.410 | 0.612 | 0.701 | 0.801 | 0.856 |
| 2 | 0.401 | 0.611 | 0.693 | 0.793 | 0.823 |
| 3 | 0.421 | 0.632 | 0.721 | 0.812 | 0.842 |
| 4 | 0.425 | 0.625 | 0.688 | 0.801 | 0.825 |
| 5 | 0.416 | 0.601 | 0.701 | 0.812 | 0.831 |

As can be seen from the results presented in Table 1 herein above, when the reaction time with monochloro acetic acid is four hours or more it is possible to produce a soluble trauma-healing hemostatic cellulose having a degree of substitution of 0.5% or more. Consequently, it is possible to control the degree of carboxymethyl group substitution by controlling the reaction time with monochloro acetic acid.

Next, in test example 2, the method of preparation of soluble trauma-healing hemostatic cellulose fibers containing coagulation protein is explained, being a method for the application of coagulation protein to soluble trauma-healing hemostatic cellulose fibers and natural or regenerated cellulose fibers. There are two different methods of imparting coagulation protein, one of which is the application and the other one the chemical bonding method, and each will be explained herein below.

First, while the soluble trauma-healing hemostatic cellulose fibers are soluble in water, in the case of an aqueous solution containing 60% of ethanol or more the fiber will not dissolve and can thus be preserved as fiber so that the application method may consist of a procedure by which a soluble trauma-healing hemostatic cellulose fiber containing coagulation protein is obtained by application in such a manner that 0.2 mL of a 60% ethanol solution containing, as coagulation proteins, 5 mg of fibrinogen, 1.5 units of thrombine, and 8 units of blood coagulation factor XIII, is uniformly sprayed on to 15.6 mg (1 cm$^2$) of soluble trauma-healing hemostatic cellulose fiber prepared in accorance with the embodiment described above (with a reaction time of 14 hours with monochloro acetic acid) while allowing to dry with a fan.

Conversely, the chemical bonding method takes place by a procedure involving the use of carbodiimide in such a manner that 15.6 mg of the soluble trauma-healing hemostatic cellulose fiber (fiber obtained by reaction with monochloroacetic acid for 14 hours) produced in accordance with the afore-described embodiment is introduced into a 5 mL capacity glass test tube and after addition of 1 mL of a 60% ethanol solution, 38 mg of 1-ethyl-3-(3-dimethyl amino propyl) carbodiimide is added with subsequently stirring at 30 degrees C. for 2 hours, whereupon the reaction solution is removed and the soluble trauma-healing hemostatic cellulose fiber treated with said carbodiimide is washed three times with 3 mL of a 60% ethanol solution. Next, addition is made thereto of 1 mL of a 60% ethanol solution containing, as coagulation proteins, 5 mg of fibrinogen, 1.5 units of thrombin, and 8 units of blood coagulation factor XIII for reaction at 30 degrees C. for 2 hours. In order to block the unreacted carboxyl groups, addition is made of 29 mg of L-lysine and after allowing to react at 30 degrees C. for 1 hours, the reaction solution is removed and the post-reaction soluble trauma-healing hemostatic cellulose fiber is washed three times with 3 mL of a 60% ethanol solution and once with 3 mL of a 95% ethanol solution. Following this, said soluble trauma-healing hemostatic cellulose fiber is dried at 50 degrees C. for five minutes to obtained a soluble trauma-healing hemostatic cellulose fiber with chemically bonded coagulation protein.

Following this, the solubility of the coagulation protein-containing soluble trauma-healing hemostatic cellulose fiber in a 0.95% sodium chloride (salt) solution and in pure water is measured as a third test example in order to ascertain the solubility of the coagulation protein-containing soluble trauma-healing hemostatic cellulose fiber obtained by either of the aforesaid method, namely, surface application and chemical bonding. The method by which these measurements are carried out is to add 0.1 g of the coagulation protein-containing soluble trauma-healing hemostatic cellulose fiber obtained by either of said methods 100 mL of an 0.95% aqueous salt solution and an equal volume of pure water, respectively, (so that the concentration of said fiber becomes 0.1 w/v %) and measure by visual inspection the time required until the insoluble parts have completely disappear while continuing to stir at 25 degrees C. The results are reported in Table 2.

TABLE 2

| Adjustment Method | Denier No. of coagulation protein-containing soluble trauma-heeling hemostatic cellulose fiber | Time required until completely dissolved (minutes) | |
|---|---|---|---|
| | | Pure water | 0.95 saline solution |
| Surface application | 1 | 10 | 18 |
| | 2 | 11 | 19 |
| | 3 | 9 | 17 |
| | 4 | 12 | 17 |
| | 5 | 10 | 19 |
| Chemical bonding | 1 | 9 | 19 |
| | 2 | 11 | 19 |
| | 3 | 10 | 18 |
| | 4 | 9 | 17 |
| | 5 | 11 | 19 |

As can be seen from the results presented in Table 2 herein above, coagulation protein-containing soluble trauma-healing hemostatic cellulose fiber in accordance with the invention of this Application is readily and completely soluble, without fail, in pure water and in saline water regardless of whether said coagulation protein is imparted by way of surface application or by chemical bonding methods.

Given as a fourth test example is the measurement of the 350 nm absorption degree using an ultraviolet spectrophotometer U-3210 (manufactured by Hitachi, Ltd.) in order to ascertain the fibrimonomer coagulation activity of the coagulation protein-containing soluble trauma-healing hemostatic cellulose fiber obtained by either of the for said method, namely, surface application and chemical bonding. For the measurement conducted in the presence of the 1 w/v % coagulation protein-containing soluble trauma-healing hemostatic cellulose fiber obtained by either of the aforesaid method (namely, surface application and chemical bonding), 20 µL of fibrimonomer (A280 nm=6)dissolved in 20 mmol/L of acetic acid was added to 500 µL of 20 mmol/L imidazol buffer solution (pH7.4) containing 0.15 mol/L of sodium chloride (NaCl) in the presence of the soluble trauma-healing hemostatic cellulose fiber (that is, soluble trauma-healing hemostatic fiber obtained without imparting coagulation protein and in the absence of soluble trauma-healing hemostatic cellulose fiber (control), and 20 seconds after of fibrinomer 350 nm absorptivity was measured every 30 seconds for 25 minutes. The results of these measurements are reported in FIG. 1.

Figure 1:
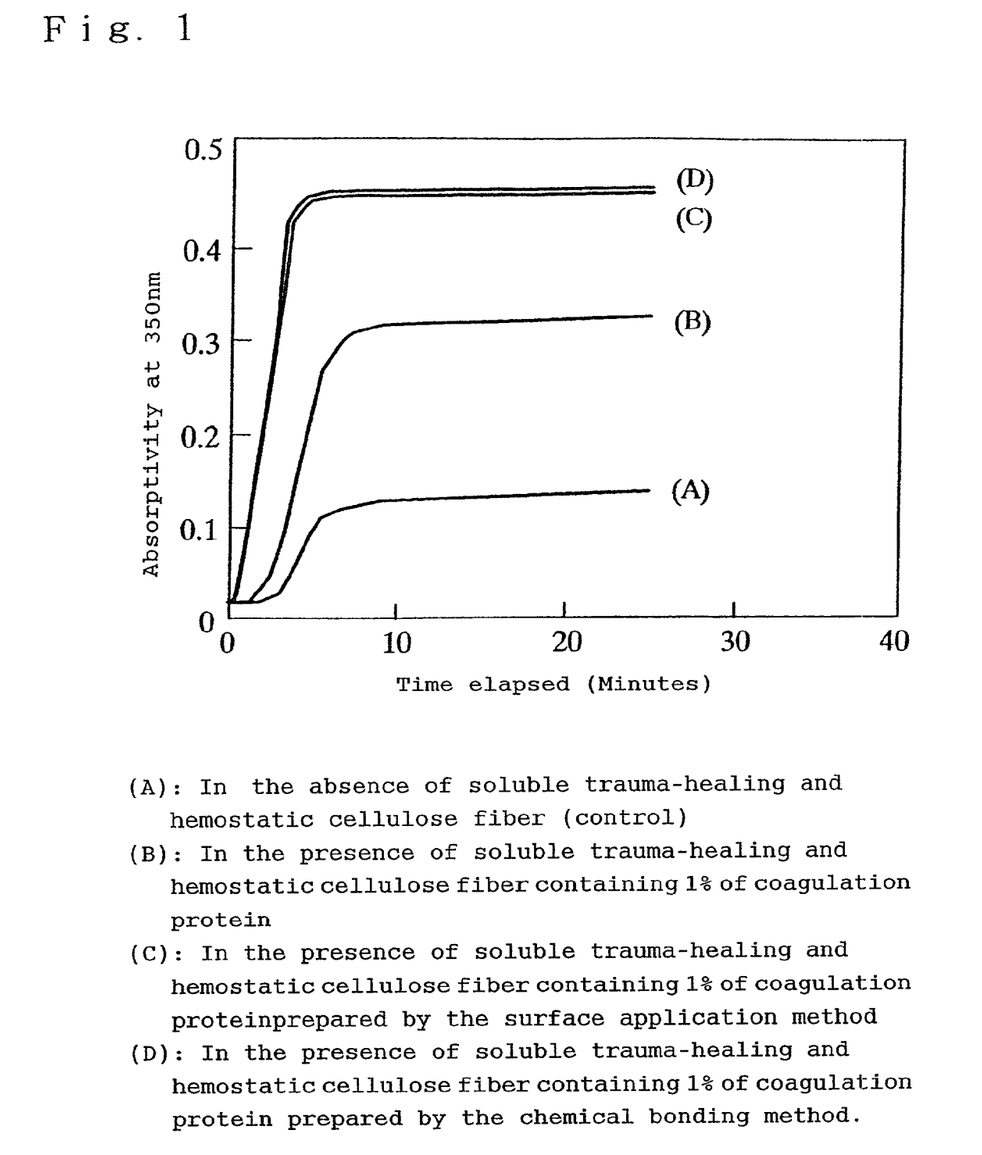
FIG. 1 shows the relationship between absorption and time obtained by measuring the absorption indicating the effect of the soluble trauma-healing hemostatic cellulose containing coagulation protein prepared by the two methods being application and chemical bonding methods with respect to the fibrimonomer coagulation reaction.

As can be seen from the results assembled in FIG. 1, the coagulation protein-containing soluble trauma-healing hemostatic cellulose fiber is capable of substantially promoting the coagulation of fibrinomer, regardless of whether said coagulation protein is imparted by way of surface application or by chemical bonding methods, and it can be recognized furthermore, that the fibrinomer coagulation activity is much superior as compared with a soluble trauma-healing hemostatic cellulose fiber to which no coagulation protein has been imparted.

Figure 2:
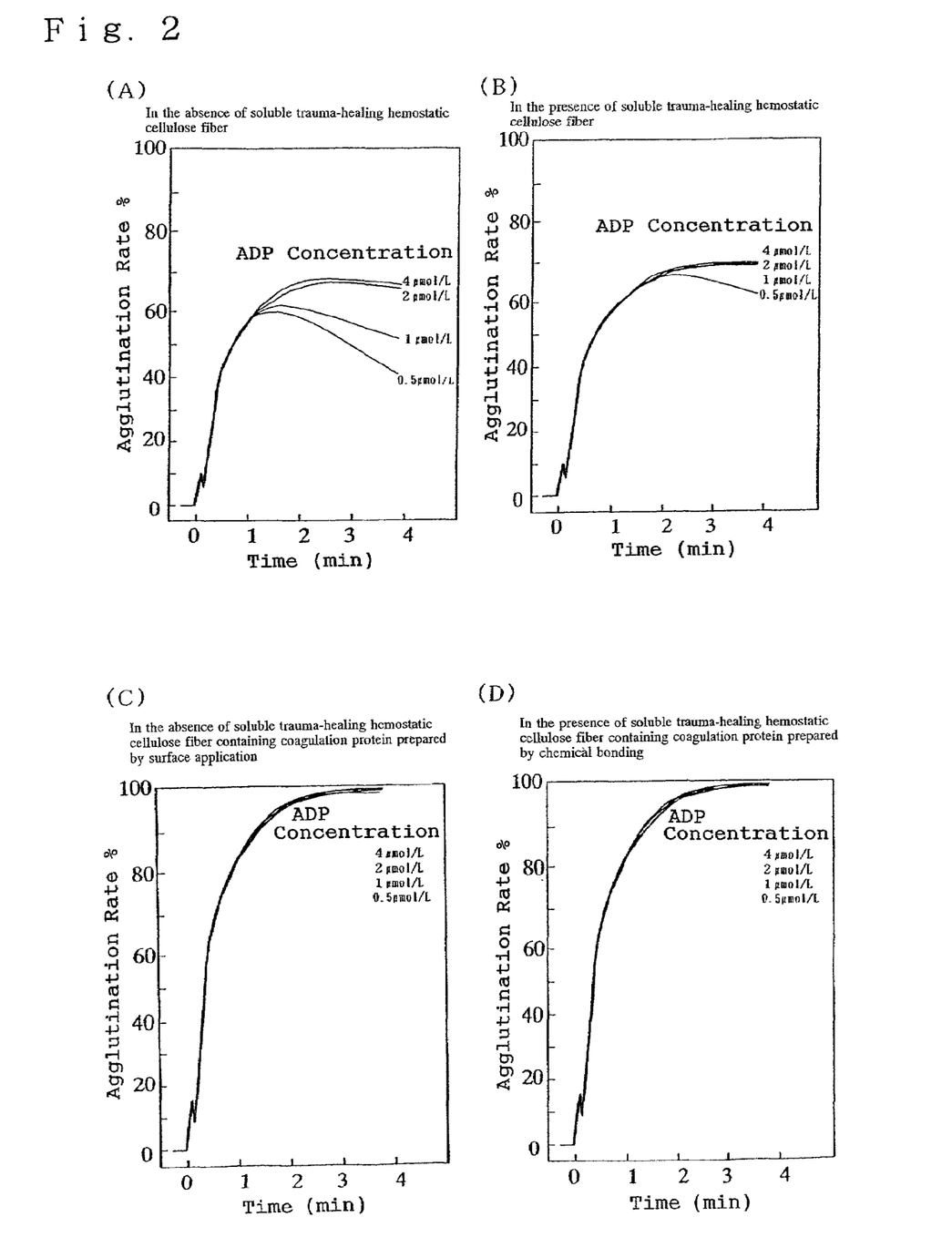

Next, in test example 5, the platelet agglutination ability has been measured using a platelet agglutination test unit (manufactured by Mebanics) in order to ascertain the platelet agglutination promoting activity of the coagulation protein-containing soluble trauma-healing hemostatic cellulose fiber obtained by either of the aforesaid methods, namely, surface application and chemical bonding, and to establish the significantly superior platelet agglutination promoting activity of the aforesaid coagulation protein-containing soluble trauma-healing hemostatic cellulose fiber as compared with the soluble trauma-healing hemostatic cellulose fiber to which no coagulation protein has been imparted. For the measurement of the platelet agglutination ability, 20 mmol/L imidazol buffer solution containing 0.15 mol/L of sodium chloride (NaCl) in the presence of the soluble trauma-healing hemostatic cellulose fiber (that is, soluble trauma-healing hemostatic cellulose fiber obtained without imparting coagulation protein and in the absence of soluble trauma-healing hemostatic cellulose fiber, was mixed with platelet-rich plasma at a ratio of 1:1 and adenosine diphosphate (ADP) was added at concentrations corresponding to its function as a platelet agglutination agent to determine the platelet agglutination ability by measuring the turbidity of the reaction solution. The results of the measurements are presented in Table 3 and

TABLE 3

| | Channel No. | ADP concentration μmol/L | Max. agglutination rate (%) | Expression time (min) | 5.0 minute value of agglutination (%) | 5.0 minute area | Separation rate w (%) |
|---|---|---|---|---|---|---|---|
| In the absence of soluble trauma-healing hemostatic cellulose fiber | 1 | 0.5 | 63 | 1.9 | 52 | 2795 | 38 |
| | 2 | 1.0 | 62 | 2.7 | 57 | 2783 | 20 |
| | 3 | 2.0 | 66 | 2.7 | 66 | 2973 | 10 |
| | 4 | 4.0 | 65 | 3.7 | 65 | 2839 | 3 |
| In the presence of soluble trauma-healing hemostatic cellulose fiber | 5 | 0.5 | 65 | 3.7 | 64 | 2910 | 8 |
| | 6 | 1.0 | 68 | 6.1 | 68 | 2943 | 0 |
| | 7 | 2.0 | 69 | 6.5 | 68 | 2929 | 0 |
| | 8 | 4.0 | 68 | 6.5 | 68 | 2929 | 0 |
| In the absence of soluble trauma-healing hemostatic cellulose fiber containing coagulation protein prepared by surface application | 9 | 0.5 | 99 | 10 | 95 | 2910 | 0 |
| | 10 | 1.0 | 97 | 9.5 | 96 | 2950 | 0 |
| | 11 | 2.0 | 94 | 9.8 | 98 | 2960 | 0 |
| | 12 | 4.0 | 95 | 9.7 | 92 | 2930 | 0 |
| In the presence of soluble trauma-healing hemostatic cellulose fiber containing coagulation protein prepared by chemical bonding | 13 | 0.5 | 95 | 9.9 | 94 | 2940 | 0 |
| | 14 | 1.0 | 96 | 9.7 | 94 | 2950 | 0 |
| | 15 | 2.0 | 99 | 9.9 | 97 | 2940 | 0 |
| | 16 | 4.0 | 98 | 9.8 | 95 | 2970 | 0 |

As can be seen from the results presented in Table 3 and FIG. 2, the coagulation protein-containing soluble trauma-healing hemostatic cellulose fiber is capable of substantially promoting platelet agglutination, regardless of whether said coagulation protein is imparted by way of surface application or by chemical bonding methods, and it can be recognized furthermore, that the platelet agglutination activity is much superior as compared with a soluble trauma-healing hemostatic cellulose fiber to which no coagulation protein has been imparted.

Next, in test example 6, the cell adhesion ability has been measured by determining the adhered cell count in a given field of view in order to ascertain the cell adhesion promoting activity of the coagulation protein-containing soluble trauma-healing hemostatic cellulose fiber obtained by either of the aforesaid methods, namely, surface application and chemical bonding, and to establish the cell adhesion promoting activity of the aforesaid coagulation protein-containing soluble trauma-healing hemostatic cellulose fiber and to demonstrate the superior cell adhesion ability thereof as compared with the soluble trauma-healing hemostatic cellulose fiber to which no coagulation protein has been imparted. For this purpose, the adhered cell count upon addition of the respective soluble trauma-healing hemostatic cellulose fiber containing 1 w/v % coagulation protein imparted by either of said methods, and the adhered cell count upon addition of soluble trauma-healing hemostatic cellulose fiber (that is, soluble trauma-healing hemostatic cellulose fiber not containing coagulation protein), and the adhered cell count without addition of soluble trauma-healing hemostatic cellulose fiber were determined. The measurement of the adhered cell count was made in such a manner that 96 well plates were covered with the cell adhesion proteins fibrinectin, vitronectin, laminin, collagen and fibrin, respectively, at the various concentrations, and that 5,000 NIH-3T3 were then introduced thereon to determine the respective adhesion protein concentrations at which no cell adhesion activity is in evidence by determining the given adhered cell count in a given field of view after six hours and by determining the adhered cell count in a given field of view following the addition of 1 w/v % coagulation protein-containing soluble trauma-healing hemostatic cellulose fiber obtained by either of the aforesaid method or soluble trauma-healing hemostatic cellulose fiber, respectively, and, alternatively, without any addition whatsoever. The results of these measurements are reported in Table 4.

TABLE 4

| | | Adhered cell count | | | |
|---|---|---|---|---|---|
| Cell adhesion protein | Concentration of cell adhesion protein (ug/mol) | Without addition of soluble trauma-healing hemostatic cellulose fiber | With addition of soluble trauma-healing hemostatic cellulose fiber | With addition of soluble trauma-healing hemostatic cellulose fiber containing coagulation protein prepared by surface application | With addition of soluble trauma-healing hemostatic cellulose fiber containing coagulation protein prepared by chemical bonding |
| Fibronectin | 0.1 | 20 | 80 | 320 | 313 |
| Vvitronectin | 0.5 | 10 | 60 | 295 | 290 |
| Laminin | 0.1 | 12 | 56 | 290 | 300 |
| Collagen I | 0.1 | 5 | 60 | 289 | 285 |
| Collagen III | 0.1 | 8 | 62 | 292 | 296 |
| Fibrin | 0.1 | 10 | 60 | 290 | 299 |

As can be seen from the results presented in Table 4, the coagulation protein-containing soluble trauma-healing hemostatic cellulose fiber exhibits a substantially higher adhered cell count, regardless of whether said coagulation protein is imparted by way of surface application or by chemical bonding methods, and it can thus be recognized that said coagulation protein-containing soluble trauma-healing hemostatic cellulose fiber possess a cell adhesion promoting activity, and that, furthermore, the cell adhesion promoting activity of said coagulation protein-containing soluble trauma-healing hemostatic cellulose fiber is significantly superior to that of the soluble trauma-healing hemostatic cellulose fiber to which no coagulation protein has been imparted.

Next, in test example 7, measurements have been conducted in order to determine the blood-stilling or hemostatic effect and the trauma-healing effect by using coagulation protein-containing soluble trauma-healing hemostatic cellulose fiber obtained by either of the aforesaid methods, namely, surface application and chemical bonding, on the trauma site, and in order to establish the substantially superior blood-stilling or hemostatic effect and the trauma-healing effect thereof as compared with the soluble trauma-healing hemostatic cellulose fiber to which no coagulation protein has been imparted. For this purpose, the time required for hemostasis to occur upon administration to the trauma site of the respective soluble trauma-healing hemostatic cellulose fiber containing 1 w/v % coagulation protein imparted by either of said methods and the extent of healing of the trauma, the time required for hemostasis to occur upon administration to the trauma site of the soluble trauma-healing hemostatic cellulose fiber not containing coagulation protein and the extent of healing of the trauma site, and the time required for hemostasis to occur without administration to the trauma site of the respective soluble trauma-healing hemostatic cellulose fiber and the extent of healing of the trauma site were determined. The hemostasis time was determined by resecting 1 cm×1 cm square patches of liver from 10 rats and attaching to the trauma site coagulation protein-containing soluble trauma-healing hemostatic cellulose fiber and soluble trauma-healing hemostatic cellulose fiber, respectively, and attaching no soluble trauma-healing hemostatic cellulose fiber (whatsoever), respectively, to measure the time required for hemostasis to occur (seconds), whereby a comparison was made with the hemostasis effect associated with the untreated trauma and that associated with the fiber to which no coagulation protein had been imparted; and, furthermore, the extent of healing was determined by attaching to the trauma site the respective soluble trauma-healing hemostatic cellulose fiber containing coagulation protein imparted by either of said methods, closing the abdominal section after the hemostatis time had been measured, performing laparotomy one month later and taking a pathology section of the trauma site for preparation and microscopic observation for visual assessment of the degree of healing. The results of the measurements are reported in Table 5. For the determination of the extent of healing of the trauma site, the specimens equivalent to the normal condition were marked with the ⊙ sign, those exhibiting some slight inflammation with the ○ sign and those showing complete healing of the inflammatory processes with the X sign.

TABLE 5

|  | Rats No. | | | | | | | | | | Mean | CV |
| --- | --- | --- | --- | --- | --- | --- | --- | --- | --- | --- | --- | --- |
|  | 1 | 2 | 3 | 4 | 5 | 6 | 7 | 8 | 9 | 10 | | |
| Hemostasis time (secs.) without treatment using soluble trauma-healing hemostatic cellulose fiber | 152 | 141 | 180 | 160 | 120 | 150 | 120 | 137 | 165 | 201 | 153 | 16.7% |
| Hemostasis time (secs.) with treatment using soluble trauma-healing hemostatic cellulose fiber | 29 ⊙ | 32 ⊙ | 31 ⊙ | 37 ⊙ | 34 ⊙ | 35 ⊙ | 32 ⊙ | 27 ⊙ | 35 ⊙ | 35 ⊙ | 33 | 9.5% |
| Hemostasis time (secs.) with treatment using hemostatic cellulose fiber containing coagulation protein prepared by surface application | 10 ⊙ | 12 ⊙ | 13 ⊙ | 11 ⊙ | 8 ⊙ | 9 ⊙ | 12 ⊙ | 11 ⊙ | 10 ⊙ | 9 ⊙ | 11 | 15.1% |
| Hemostasis time (secs.) with treatment using hemostatic cellulose fiber containing coagulation protein prepared by chemical bonding | 11 ⊙ | 10 ⊙ | 12 ⊙ | 9 ⊙ | 12 ⊙ | 11 ⊙ | 8 ⊙ | 9 ⊙ | 10 ⊙ | 12 ⊙ | 10 | 13.7% |

As can be seen from the results presented in Table 5, soluble trauma-healing hemostatic cellulose fiber has a substantial blood-stilling or hemostatic effect, and the ten rats treated with soluble trauma-healing hemostatic cellulose fiber exhibited a virtually complete healing without any signs of inflammation whatsoever, and it can therefore be recognized that coagulation protein-containing soluble trauma-healing hemostatic cellulose fiber possess a substantial hemostatic and trauma-healing effect as compared with soluble trauma-healing hemostatic cellulose, regardless of whether said coagulation protein is imparted by way of surface application or by chemical bonding methods.

The coagulation protein-containing soluble trauma-healing hemostatic cellulose fiber produced as described herein above and in accordance with the invention of this Application absorbs both blood and tissue fluid when applied to the trauma site, regardless of whether said coagulation protein is imparted by way of surface application or by chemical bonding methods, increases the concentration and viscosity of the blood and the tissue fluid, and generates potent fibrin agglutinates under the action of the fibrinogen, thrombin and coagulation factor XIII contained in said coagulation protein-containing soluble trauma-healing hemostatic cellulose fiber, thereby exhibiting a powerful blood-stilling or hemostatic effect in such manner as to reduce the flow (rate) of the blood and tissue fluid; and exihiting, furthermore, a blood-stilling or hemostatic effect by assisting platelet adhesion to, and platelet agglutination in, the trauma site.

Moreover, coagulation protein-containing soluble trauma-healing hemostatic cellulose fiber in accordance with the inventions of the present Application interacts with the adhesion proteins such as fibronectin and promotes the growth of fibroblasts which play an important role in the trauma healing process.

While the explanations concerning the test examples described herein above refer to the sodium salt of the coagulation protein-containing soluble trauma-healing hemostatic cellulose fiber, the invention according to the present Application is not limited thereto but may, without any limitation whatsoever, also refer to the calcium salt of the coagulation protein-containing soluble trauma-healing hemostatic cellulose fiber or to mixtures of a multiplicity of salts thereof.

Whereas, furthermore, all of the explanations concerning the test examples described herein above refer to a coagulation protein-containing soluble trauma-healing hemostatic cellulose fiber formed into a fabric the invention according to the present Application is not limited thereto but may naturally also apply to a product formed into a powder by subjecting the threadlike or fabric-like coagulation protein-containing soluble trauma-healing hemostatic cellulose fiber to a pulverization treatment or to a product formed into a gauze material by subjecting the threadlike or fabric-like coagulation protein-containing soluble trauma-healing hemostatic cellulose fiber to a shoddy wool treatment, provided that any such coagulation protein-containing soluble trauma-healing hemostatic cellulose fiber product does exhibit a trauma-healing and hemostatic effect as being the purpose of the present invention.

As explained herein above, the coagulation protein-containing soluble trauma-healing hemostatic cellulose fiber in accordance with the invention of the present Application has an extremely speedy blood-stilling or hemostatic effect, presents a speedy in-vivo absorption behavior virtually without giving rise to any inflammatory reactions and exhibits a high trauma-healing effect.

Furthermore, the coagulation protein containing soluble trauma-healing and hemostatic material in accordance with the invention of the present Application is capable of producing a trauma-healing effect based on its ability to promote hemostasis and cell adhesion in the trauma site at high efficiency; wherefore it is eminently effective a a hemostatic and trauma-healing material for both internal and external application and has a significant scope for potential application in a wide range of uses as a trauma-covering hemostatic material capable of enhancing the healing effect of the trauma locus.

The invention claimed is:

1. A soluble trauma-healing hemostatic cellulose fiber, comprising a natural or regenerated cellulose fiber that has been partially carboxymethylated to an extent such that degree of substitution of the hydroxyl groups in the glucose units constituting the cellulose molecule is 0.5-less than 1.0, wherein three types of coagulation proteins being fibrinogen, thrombin and coagulation factor XIII are applied or chemically bonded to said fiber followed by drying, such that said fiber possesses activity for accelerating a coagulation reaction of fibrin monomers converted from fibrinogen with thrombin and possesses activity for stabilizing agglutinates by cross-linking reaction with the coagulation factor XIII.

2. The fiber of claim 1, wherein the coagulation protein is imparted by surface application to the carboxymethylated natural or regenerated cellulose fiber.

3. The fiber of claim 2, wherein the coagulation protein is applied by spraying a solution thereof onto the fiber.

4. The fiber of claim 2, wherein a mixture of all three proteins is imparted in a single application.

5. The fiber of claim 2, wherein said three proteins are consecutively imparted in individual applications.

6. The fiber of claim 1, wherein said protein is imparted by chemical bonding to the carboxymethylated natural or regenerated cellulose fiber.

7. The fiber of claim 6, wherein said fiber is treated with carbodiimide prior to the reaction with the protein.

8. The fiber of claim 6, wherein a mixture of all three proteins is chemically bonded in a single pass.

9. The fiber of claim 6, wherein said three proteins are chemically bonded in consecutive passes.

10. The fiber of claim 1, wherein the fiber is pulverized after the protein is imparted.

11. The fiber of claim 5, wherein a plurality of said thus-treated fibers are individually pulverized and then mixed.

12. The fiber of claim 11, wherein the proteins are applied by spraying solutions thereof.

13. The fiber of claim 9, wherein a plurality of said thus-treated fibers are individually pulverized and then mixed.

14. The fiber of claim 13, wherein the fibers are treated with carbodiimide reagent prior to the chemical reaction.

15. A drawn thread array having a number of single threads of the fiber according to claim 1 loosely twisted together.

16. A woven fabric comprising a plain or twill woven array of claim 15.

17. The fabric of claim 16, wherein the arrays of the drawn fibers have a thickness of 20-100 Denier.

18. Gauze-like material obtained by shoddy wool treatment of fibers of claim 1.

19. A method of producing a soluble trauma-healing hemostatic cellulose fiber, comprising the steps of:
    treating a natural or regenerated cellulose fiber with an aqueous sodium hydroxide solution,
    reacting the thus-treated fiber with a monochloro acetic acid solution for carboxymethylation to an extent such that degree of substitution of hydroxyl groups of the glucose units constituting the cellulose molecule (etherification degree) is 0.5 to less than 1.0,
    subsequently refining the fiber and then imparting or chemical bonding three coagulation proteins which are fibrinogen, thrombin and coagulation factor XIII, to the refined cellulose fiber, and
    then drying the fiber,
    whereby said fiber possesses activity for accelerating a coagulation reactionof fibrin monomers converted from fibrinogin with thrombin, and possesses activity for stabilizing the agglutinates by the cross-linking reaction with the coagulation factor XIII.

20. The method of claim 19, wherein the proteins are imparted by spraying a solution of all three proteins in a single pass.

21. The method of claim 19, wherein the proteins are imparted by spraying respective solutions of each said protein in consecutive passes.

22. The method of claim 19, wherein the proteins are imparted by chemical bonding with a single solution of all three proteins in a single pass.

23. The method of claim 19, wherein the proteins are imparted by chemical bonding with respective solutions of each said protein in consecutive passes.

24. The method of claim 19, comprising the additional step of pulverizing the fiber after drying.

25. The method of claim 21, comprising the additional step of after drying, pulverizing and then mixing thus-produced fibers.

26. The method of claim 19, wherein the reaction with monochloro acetic acid is carried out for 4-18 hours.

27. The method of claim 19, comprising the additional step of loosely twisting threads of said fiber together to form a drawn thread array.

28. The method of claim 27, comprising the additional step of plain or twill weaving the drawn thread array to form a woven fabric.

29. The method of claim 27, wherein the drawn fiber array is formed with a thickness of 20-100 Denier.

30. The method of claim 19, comprising the additional step of carrying out shoddy wool treatment of the fibers to form a gauze-like material.

31. The fiber of claim 3 possessing fibrinomer absorptivity at 350 nm of at least 0.4 after 3 minutes of application.

32. The fiber of claim 6 possessing fibrinomer absorptivity at 350 nm of at least 0.4 after 3 minutes of application.

33. The fiber of claim 3 possessing a maximum platelet agglutination rate of at least about 94% and an agglutination % 5 minutes after addition of at least about 92%.

34. The fiber of claim 6 possessing a maximum platelet agglutination rate of at least about 94% and an agglutination % 5 minutes after addition of at least about 92%.

35. The fiber of claim 3 possessing an adhered cell count for fibronectin, vitronectin, laminin, collagen or fibrin of at least about 285 after 6 hours of application.

36. The fiber of claim 6 possessing an adhered cell count for fibronectin, vitronectin, laminin, collagen or fibrin of at least about 285 after 6 hours of application.

37. The fiber of claim 3, possessing a mean hemostasis time of about 10-11 seconds after application to an approximately 1 square cm. trauma site in livers of rats.

38. The fiber of claim 6, possessing a mean hemostasis time of about 10-11 seconds after application to an approximately 1 square cm. trauma site in livers of rats.

* * * * *